United States Patent [19]

Audiau et al.

[11] Patent Number: 4,980,356
[45] Date of Patent: Dec. 25, 1990

[54] 2-IMINO-6-POLYFLUOROALKOXYBENZO-THIAZOLE DERIVATIVES, AND PHARAMACEUTICAL COMPOSITIONS CONTAINING THEM AND THEIR TREATMENT OF MEDICAL CONDITIONS ASSOCIATED WITH THE EFFECTS OF GLUTAMATE

[75] Inventors: François Audiau, Charenton Le Pont; Claude Gueremy, Houilles; Patrick Jimonet, Villepreaux; Serge Mignani, Livry, all of France

[73] Assignee: Rhone-Poulenc Sante, France

[21] Appl. No.: 449,810

[22] Filed: Dec. 13, 1989

[30] Foreign Application Priority Data

Dec. 15, 1988 [FR] France ................................ 88 16547
Jul. 13, 1989 [FR] France ................................ 89 09482

[51] Int. Cl.$^5$ .................. C07D 403/12; C07D 417/12; C07D 277/82; A61K 31/505
[52] U.S. Cl. .................... 514/269; 514/338; 514/370; 544/315; 544/319; 546/270; 548/161
[58] Field of Search .................. 548/161; 546/270; 544/315, 319; 514/338, 370, 269

[56] References Cited
U.S. PATENT DOCUMENTS 4,929,623 5/1990 Abe et al. ............................ 548/161

Primary Examiner—Alan L. Rotman
Assistant Examiner—Joseph K. McKane
Attorney, Agent, or Firm—Morgan & Finnegan

[57] ABSTRACT

Compounds of formula:

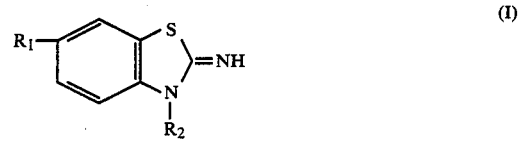

(I)

and their salts, in which $R_1$ represents polyfluoroalkoxy, and $R_2$ represents alkyl, alkenyl (3-6 C), [cycloalkyl (3-6 C)]-alkyl, carbamoylalkyl, dialkylcarbamoylalkyl, acylaminoalkyl, phenylthioalkyl, hydroxyalkyl, cyanoalkyl, sulphamoylethyl, N-alkylsulphamoylethyl, pyridylthioalkyl, pyridiylalkylthioalkyl, pyridylsulphinylalkyl, alkynyl (3-6 C), phenylsulphinylalkyl, halophenylthioalkyl, (2,2,2-trifluoroethylthio)alkyl, 2-dialkylaminopropyl, pyrimidinylsulphinylalkyl, pyridylalkylsulphinylalkyl, halophenylsulphinylalkyl or (2,2,2-trifluoroethylsulphinyl)alkyl are useful in the treatment of medical conditions associated with the effects of glutamate.

6 Claims, No Drawings

2-IMINO-6-POLYFLUOROALKOXYBENZOTHIAZOLE DERIVATIVES, AND PHARAMACEUTICAL COMPOSITIONS CONTAINING THEM AND THEIR TREATMENT OF MEDICAL CONDITIONS ASSOCIATED WITH THE EFFECTS OF GLUTAMATE

The present invention provides 2-imino-6-polyfluoroalkoxybenzothiazole derivatives of formula:

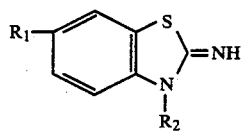

and their salts, in which
$R_1$ represents polyfluoroalkoxy, and
$R_2$ represents alkyl, alkenyl (3–6 C), [cycloalkyl(-3–6C)]alkyl, carbamoylalkyl, dialkylcarbamoylalkyl, acylaminoalkyl, phenylthioalkyl, hydroxyalkyl, cyanoalkyl, sulphamoylethyl, N-alkylsulphamoylethyl, pyridylthioalkyl, pyridylalkylthioalkyl, pyridylsulphinylalkyl, alkynyl (3–6 C), phenylsulphinylalkyl, halophenylthioalkyl, (2,2,2-trifluoroethylthio)alkyl, 2-dialkylaminopropyl, pyrimidinylsulphinylalkyl, pyridylalkylsulphinylalkyl, halophenylsulphinylalkyl or (2,2,2-trifluoroethylsulphinyl)alkyl.

Except where otherwise stated, in the definitions above and those mentioned below, the alkyl radicals and alkyl and alkoxy portions contain 1 to 4 carbon atoms each in a straight or branched chain. The addition salts of the compounds of formula (I) with inorganic or organic acids are part of the invention.

Preferred polyfluoroalkoxy radicals are trifluoromethoxy, pentafluoroethoxy, 2,2,2-trifluoroethoxy, 1,1,2,2-tetrafluoroethoxy and 2,2,3,3,3-pentafluoropropoxy.

The compounds of formula (I) in which $R_2$ represents cyanoalkyl, carbamoylalkyl, sulphamoylethyl or N-alkylsulphamoylethyl, may be obtained by the action of bromine and an alkali metal thiocyanate on a compound of formula:

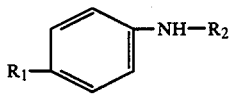

in which $R_1$ has the same meanings as in the formula (I) and $R_2$ has the same meaning as that given above.

This reaction is generally performed in acetic acid, at a temperature of approximately 20° C. Potassium thiocyanate is preferably used as the alkali metal thiocyanate.

The derivatives of formula (II) in which $R_2$ represents cyanoalkyl may be obtained by the action of a 4-polyfluoro-alkoxyaniline on a derivative of formula:

Hal—$R_2$ (III)

in which Hal represents halogen and $R_2$ represents cyanoalkyl.

This reaction is generally performed in an inert organic solvent or water, at a temperature between 50° C. and the boiling point of the solvent.

4-Polyfluoroalkoxyanilines may be obtained by application or adaptation of the methods described by W. A. SHEPPARD, J. Org. Chem., 29,1 (1964); in Beilstein 12,1166 and in U.S. Pat. Nos. 3,920,444, 2,436,100, DE No. 3,195,926, DE No. 2,606,982 and EP No. 205,821.

The derivatives of formula (II) for which $R_2$ denotes a carbamoylalkyl may be obtained from the corresponding nitriles by any method known to those skilled in the art enabling a nitrile to be converted into an amide.

It is preferable to employ sulphuric acid, at a temperature of between 60° C. and 100° C.

The derivatives of formula (II) for which $R_2$ represents sulphamoylethyl or N-alkylsulphamoylethyl may be obtained by the action of a compound of formula:

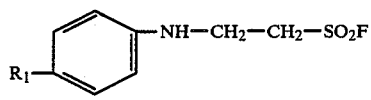

in which $R_1$ has the same meanings as in the formula (I), with ammonium hydroxide or an alkylamine.

This reaction is generally performed in an inert solvent such as a ketone (acetone, methyl ethyl ketone, etc.) or an aromatic solvent (benzene, toluene, etc.), at a temperature between 30° C. and the boiling point of the solvent.

The derivatives of formula (IV) may be obtained by the action of a 4-polyfluoroalkoxyaniline on vinylsulphonyl fluoride. This reaction is preferably performed in an inert solvent such as dimethylformamide, at a temperature in the region of 20° C.

Vinylsulphonyl fluoride may be obtained according to the method described by J. J. KRUTAK et al., J. Org. Chem., 44(22), 3847( 1979).

The derivatives of formula (I) in which $R_2$ represents pyridylthioalkyl or pyridylalkylthioalkyl may be prepared by the action of a compound of formula:

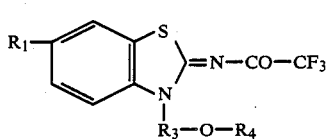

in which $R_1$ has the same meanings as in the formula (I), $R_3$ represents alkylene (1–4 C) and $R_4$ represents a reactive group such as a methanesulphonyl or p-toluenesulphonyl radical, on a mercaptopyridine or a pyridylalkyl mercaptan, followed by hydrolysis of the product obtained.

This reaction is generally performed in an inert solvent such as dimethylformamide, at a temperature in the region of 20° C. The hydrolysis is accomplished by means of a base such as concentrated ammonia solution, at the boiling point of the reaction medium.

The derivatives of formula (V) may be prepared by the action of a compound of formula:

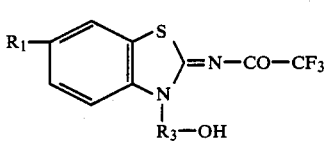

in which $R_1$ and $R_3$ have the same meanings as in the formula (V), on methanesulphonyl chloride or p-toluenesulphonyl This reaction is preferably performed either in an inert solvent such as benzene, toluene, chloroform or methylene chloride, in the presence of a tertiary amine such as triethylamine, at a temperature in the region of 20° C., or in pyridine at a temperature in the region of 0° C.

The derivatives of formula (VI) may be obtained by the action of a compound of formula:

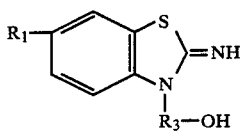

(VII)

in which $R_1$ and $R_3$ have the same meanings as in the formula (V), on ethyl trifluoroacetate.

This reaction is generally performed in an alcohol, in the presence of a tertiary base such as triethylamine, at a temperature in the region of 20° C.

The derivatives of formula (VII) may be obtained by the action of a 2-amino-6-polyfluoroalkoxybenzothiazole on an alcohol of formula:

Hal—$R_3$—OH (VIII)

in which Hal denotes a halogen atom and $R_3$ has the same meanings as in the formula (VII).

This reaction is performed in an alcohol, at the boiling point of the solvent.

2-Amino-6-polyfluoroalkoxybenzothiazoles may be prepared by application or adaptation of the method described by L. M. YAGUPOL'SKII et al., Zh. Obsch. Khim., 33(7), 2301 (1963).

The compounds of formula (I) in which $R_2$ represents alkyl, alkenyl, cycloalkylalkyl, dialkylcarbamoylalkyl, acylaminoalkyl, phenylthioalkyl, hydroxyalkyl, alkynyl, halophenylthioalkyl, (2,2,2-trifluoroethylthio)alkyl or 2-dialkylaminopropyl may be prepared by the action of an amino derivative of formula:

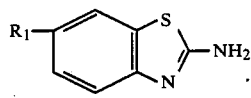

(IX)

on a compound of formula:

$R_2$—X (X)

in which formulae $R_2$ has the same meanings as above, $R_1$ has the same meanings as in the formula (I) and X denotes a reactive group such as tosyloxy radical or a halogen (preferably chlorine, bromine or iodine) atom.

This reaction is preferably performed in an inert solvent such as an alcohol, (e.g. ethanol or propanol), a ketone (e.g. acetone or methyl ethyl ketone) or dimethylformamide, at a temperature between 10° C. and the boiling point of the solvent, optionally in the presence of sodium iodide and optionally after melting the compounds of formulae (IX) and (X) at 130°–140° C.

The derivatives of formula (X) for which $R_2$ denotes an alkynyl radical may be obtained by application or adaptation of the methods described in Beilstein, 1, IV, 970 and 974.

The derivatives of formula (X) for which $R_2$ denotes a halophenylthioalkyl radical may be obtained by application or adaptation of the method described by H. P. S. CHAWLA et al., J. Med. Chem., 13(3), 480 (1970).

The derivatives of formula (X) in which $R_2$ represents (2,2,2-trifluoroethylthio)alkyl may be obtained by the action of a compound of formula:

HO—$R_2$ (XI)

in which $R_2$ has the same meanings as above, on carbon tetrachloride, in the presence of triphenylphosphine.

This reaction is generally performed at the boiling point of the reaction medium.

The derivatives of formula (XI) in which $R_2$ represents (2,2,2-trifluoroethylthio)alkyl may be obtained by application or adaptation of the method described by R. C. TERRELL et al., J. Org. Chem., 30(12), 4011 (1965).

The other compounds of formula (X) which are not commercially available may be prepared by application or adaptation of the method described by W. C. HOWELL, J. Amer. Chem. Soc., 78, 3843 (1956) and the methods described in the examples.

The compounds of formula (I) in which $R_2$ represents pyridylalkylsulphinylalkyl, phenylsulphinylalkyl, pyridylsulphinylalkyl, pyrimidinylsulphinylalkyl, halophenylsulphinylalkyl or (2,2,2-trifluoroethylsulphinyl)alkyl may be prepared by oxidation of the corresponding derivatives for which $R_2$ denotes a pyridylalkylthioalkyl, phenylthioalkyl, pyridylthioalkyl, pyrimidinylthioalkyl, halophenylthioalkyl or (2,2,2-trifluoroethylthio)alkyl.

This oxidation may be accomplished by means of m-chloroperbenzoic acid, in an alcohol, at a temperature in the region of 20° C.

The derivatives in which $R_2$ represents phenylthioalkyl may be prepared by the action of a 2-amino-6-polyfluoro-alkoxybenzothiazole on a haloalkylthioalkyl compound.

This reaction is generally performed in an organic solvent such as ethanol, propanol, methyl ethyl ketone or dimethylformamide, at a temperature between 60° C. and the boiling point of the solvent.

The derivatives in which $R_2$ represents pyrimidinylthioalkyl may be prepared by the action of a mercaptopyrimidine on a compound of formula (V).

The reaction mixtures obtained by the various processes described above are treated according to conventional physical methods (evaporation, extraction, distillation, crystallization, chromatography, etc.) or chemical methods (salt formation, etc.).

The compounds of formula (I), in free base form, can be optionally converted into addition salts with an inorganic or organic acid, by the action of such an acid in an organic solvent such as an alcohol, ketone, ether or chlorinated solvent.

The compounds of formula (I) and their salts possess advantageous pharmacological properties. These compounds are useful in the treatment of medical conditions associated with the effects of glutamate in which it is desirable to inhibit such effort at least partially. They are active with respect to glutamate-induced convulsions, and are hence useful in the treatment and prevention of convulsive phenomena, schizophrenic disorders, and in particular the deficiency forms of schizophrenia, sleep disorders, phenomena linked to cerebral ischaemia and also neurological conditions in which glutamate may be implicated, such as Alzheimer's disease, Huntington's chorea, amyotrophic lateral sclerosis and olivopontocerebellar atrophy.

The activity of the compounds of formula (I) with respect to glutamate-induced convulsions was determined according to a technique based on that of I. P. LAPIN, J. Neural. Transmission, vol. 54, 229–238 (1982); intracerebroventricular injection of glutamate being performed according to a technique based on that of R. CHERMAT and P. SIMON, J. Pharmacol. (Paris), vol. 6, 489–492) (1975). Their $ED_{50}$ does not exceed 10 mg/kg.

The compounds of formula (I) possess low toxicity. Their $LD_{50}$ is above 15 mg/kg when administered i.p. in mice.

For medicinal use, the compounds of formula (I) may be employed as they are, or in the form of pharmaceutically acceptable salts, i.e. salts which are non-toxic at the doses at which they are used.

As examples of pharmaceutically acceptable salts, the addition salts with inorganic or organic acids, such as acetate, propionate, succinate, benzoate, fumarate, maleate, oxalate, methanesulphonate, isethionate, theophyllineacetate, salicylate, sulphate, nitrate and phosphate, may be mentioned. The examples which follow illustrate the invention.

EXAMPLE 1

Bromine (3.2 g; 1 cc) is added at room temperature to 3-(4-trifluoromethoxyanilino)propionitrile (3 g) and potassium thiocyanate (7.8 g) dissolved in acetic acid (50 cc). Stirring is maintained for 12 hours at this temperature. The mixture is evaporated to dryness at 80° C. under reduced pressure (20 mm Hg; 2.7 kPa). The residue obtained is taken up with water (100 cc) and the pH is brought to 9–10 by adding concentrated sodium hydroxide (10N). After extraction with ethyl acetate (2×50 cc, washing of the combined phases with water (2×20 cc), drying over anhydrous magnesium sulphate and evaporation to dryness at 40° C. under reduced pressure (20 mm Hg; 2.7 kPa), a brown oil is isolated. This oil is dissolved in acetone (100 cc) and oxalic acid (2 g) is added. 2-Imino-3-(2-cyanoethyl)-6-trifluoromethoxy-benzothiazoline (5.5 g) is thereby isolated in the form of a monooxylate, m.p. 180° C.

3-(4-Trifluoromethoxyanilino)propionitrile may be prepared in the following manner: 4-trifluoromethoxyaniline (17.7 g) and 3-bromopropionitrile (6.7 g) in water (20 cc) are brought to reflux with stirring for 12 hours. The solution is then cooled and taken to dryness at 80° C. under reduced pressure (20 mm Hg; 2.7 kPa). The residue obtained is purified by flash chromatography on a silica column under a stream of nitrogen at moderate pressure (0.5–1.5 bars), with a mixture of cyclohexane and ethyl acetate (80:20 by volume) as eluent. A yellow oil (8.7 g) is obtained.

EXAMPLE 2

The procedure is as in Example 1, starting with 3-(4-trifluoromethoxyanilino)propionamide (4.2 g), potassium thiocyanate (6.6 g) and bromine (2.7 g; 0.85 cc) in acetic acid (50 cc). The mixture is stirred at a temperature of approximately 20° C. for 12 hours. Water (100 cc) is added and the pH is brought to 9–10 with concentrated sodium hydroxide (10N). After extraction with ethyl acetate (2×50 cc), drying of the combined organic phases over anhydrous magnesium sulphate and evaporation to dryness at 40° C. under reduced pressure (20 mm Hg; 2.7 kPa), is isolated, which solid is recrystallized in boiling acetonitrile (100 cc). 3-(2-Imino-6-trifluoromethoxy-3-benzothiazolinyl)propionamide (2.3 g), m.p. 219° C., is isolated.

3-(4-Trifluoromethoxyanilino)propionamide may be prepared in the following manner: 3-(4-trifluoromethoxyanilino)propionitrile (5.4 g), obtained in Example 1, and concentrated sulphuric acid (20 cc) are heated to 90° C. for 2 hours. After cooling to a temperature of 20° C., this solution is added to ice (250 g) and the pH is brought to 9–10 with concentrated sodium hydroxide (10N). 3-(4-Trifluoromethoxyanilino)propionamide (4.2 g), m.p. 76° C., is thereby isolated directly.

EXAMPLE 3

Bromine (2.3 g), dissolved in acetic acid (10 cc), is added in the course of approximately 15 minutes to a mixture of 2-(p-trifluoromethoxyanilino)ethanesulphonamide (4.1 g) and potassium thiocyanate (5.6 g, in the same solvent (20 cc). The reaction is continued for 15 hours at a temperature in the region of 20° C. After the addition of distilled water (50 cc), the reaction medium is neutralized with 30% strength sodium hydroxide. The precipitate formed is filtered off and then taken up in methanol (50 cc), the mixture is filtered again and the filtrate is concentrated to dryness under reduced pressure (20 mm Hg; 2.7 kPa). After formation of the hydrochloride by adding 4.2N ethereal hydrogen chloride (3.6 cc) in a mixture of ethyl ether and methanol, followed by recrystallization in absolute ethanol (50 cc), 2-(2-imino-6-trifluoro-methoxy-3-benzothiazolinyl)ethanesulphonamide hydrochloride (2.9 g), subliming at about 225° C., is obtained.

2-(p-Trifluoromethoxyanilino)ethanesulphonamide may be prepared according to the following process: 2-(p-trifluoromethoxyanilino)ethanesulphonyl fluoride (8.6 g) and 28% strength ammonium hydroxide [30 cc) in acetone (50 cc) are heated to boiling for 1 hour. After cooling of the mixture to a temperature in the region of 20° C., the acetone is evaporated off under reduced pressure (20 mm Hg; 2.7 kPa) and the organic phase extracted with ethyl acetate (3×50 cc). After drying over magnesium sulphate, concentration to dryness under reduced pressure and then chromatography on a silica column with a mixture of ethyl acetate and cyclohexane (50:50 by volume) as eluent, 2-(p-trifluoromethoxyanilino)ethanesulphonamide (5.5 g) is obtained in the form of a pinkish oil.

2-(p-Trifluoromethoxyanilino)ethanesulphonyl fluoride may be prepared in the following manner: vinylsulphonyl fluoride (11.9 g), dissolved in dimethylformamide (10 cc), is added dropwise to p-trifluoromethoxyaniline (19.1 g) dissolved in dimethylformamide (20 cc). The reaction is continued for 2 hours at a temperature in the region of 20° C. The reaction medium is added to distilled water (300 cc) and the aqueous phase extracted with ethyl ether (3×50 cc). After drying and concentration to dryness under reduced pressure (20 mm Hg; 2.7 kPa), 2-(p-trifluoromethoxyanilino)ethanesulphonyl fluoride (25.8 g) is obtained in the form of an orange-coloured oil, which is used in the crude state in the subsequent stages of synthesis.

Vinylsulphonyl fluoride may be obtained according to the method described by J. J. Krutak et al., J. Org. Chem. 44 (22) 3847 (1979).

EXAMPLE 4

The procedure is as in Example 3, starting with N-methyl-2-(p-trifluoromethoxyanilino)ethanesulphonamide (3.5 g), potassium thiocyanate (4.7 g) and bromine (2.2 g) in acetic acid (30 cc). After 18 hours at a temperature in the region of 20° C., neutralization with 30% strength sodium hydroxide and extraction with ethyl acetate, a crude product is obtained, which product is converted to a hydrochloride by adding 4.2N ethereal hydrogen chloride (3 cc) in ethanol (25 cc) and recrystallized in absolute ethanol (50 cc). The N-methyl-2-(2-imino-6-trifluoromethoxy-3-benzothiazolinyl)ethanesulphonamide hydrochloride thereby obtained (2.1 g) melts at 242° C.

N-Methyl-2-(p-trifluoromethoxyanilino)ethanesulphonamide may be prepared in the following manner: the procedure is as in Example 3 for the preparation of 2-(p-trifluoromethoxyanilino)ethanesulphonamide, but starting with 2-(p-trifluoromethoxyanilino)ethanesulphonyl fluoride (6.0 g) and 40% strength aqueous methylamine (20 cc) in acetone (30 cc). After the mixture is heated for 1 hour to boiling, the acetone is evaporated off and the organic phase extracted with ethyl acetate. The crude product obtained is purified by chromatography on a silica column with a mixture of ethyl acetate and cyclohexane (50:50 by volume) as eluent. N-methyl-2-(p-trifluoromethoxyanilino)ethanesulphonamide (3.5 g) is obtained in the form of a yellow oil, which is used in the crude state in the following reactions.

EXAMPLE 5

The procedure is as in Example 3, starting with N-ethyl-2-(p-trifluoromethoxyanilino)ethanesulphonamide (6.1 g), potassium thiocyanate (7.6 g) and bromine (3.6 g) in acetic acid (60 cc). After 18 hours at a temperature in the region of 20° C., neutralization with 30% strength sodium hydroxide and extraction with ethyl acetate, a crude product is obtained, which product is converted to a hydrochloride by adding 4.2N ethereal hydrogen chloride (5 cc) in ethanol (30 cc) and recrystallized in absolute ethanol (50 cc). N-Ethyl-2-(2-imino-6-trifluoromethoxy-3-benzothiazolinyl)ethanesulphonamide hydrochloride (3.0 g), m.p. 240° C., is thereby obtained.

N-Ethyl-2-(p-trifluoromethoxyanilino)ethanesulphonamide may be prepared as in Example 3 for the preparation of 2-(p-trifluoromethoxyanilino)ethanesulphonamide, starting with 2-(p-trifluoromethoxyanilino)ethanesulphonyl fluoride (6.0 g) and 33% strength aqueous ethylamine (20 cc) in acetone (30 cc). After heating for 1 hour to boiling, the acetone is evaporated off and the organic phase extracted with ethyl acetate. N-Ethyl-2-(p-trifluoromethoxyanilino)ethanesulphonamide (6.1 g) is thereby obtained in the form of a brown oil, which is used in the crude state in the following reactions.

EXAMPLE 6

2-(2-Trifluoroacetylimino-6-trifluoromethoxy-3-benzothiazolinyl)ethyl para-toluenesulphonate (8 g) is added to a solution, cooled to a temperature in the vicinity of 20° C., of 4-mercaptopyridine sodium salt (the solution being obtained after cessation of the evolution of gas from a solution of 4-mercaptopyridine (1.8 g) in dimethylformamide (30 cc) and a suspension of sodium hydride (0.8 g) in 50% strength dispersion in liquid paraffin, reacted for 1 hour at 50° C.). The reaction medium is stirred for 2 hours at a temperature in the region of 20° C. Ethanol (50 cc), water (10 cc) and concentrated ammonia solution (10N) (20 cc) are then added, in that order, to this solution. The solution is brought to reflux for 1 hour and cooled to a temperature in the region of 20° C. This aqueous solution is extracted with dichloromethane (2×50 cc); the organic phase is dried over anhydrous magnesium sulphate, filtered and concentrated to dryness at 40° C. under reduced pressure (20 mm Hg; 2.7 kPa). The residue obtained is purified by flash chromatography on a silica column under a stream of nitrogen at moderate pressure (0.5–1.5 bars) with ethyl acetate as eluent, and the solid obtained is treated with oxalic acid (2.4 g) and acetone (10 cc). 2-Imino-3-[2-(4-pyridylthio)ethyl]-6-trifluoromethoxybenzothiazoline (3.5 g) is isolated in the form of a dioxalate, m.p. 164° C.

2-(2-Trifluoroacetylimino-6-trifluoromethoxy-3-benzothiazolinyl)ethyl p-toluenesulphonate may be prepared according to the following process: 2-(2-trifluoroacetylimino-6-trifluoromethoxy-3-benzothiazolinyl)ethanol (19.3 g) is added gradually to p-toluenesulphonyl chloride (19.7 g) dissolved in pyridine (120 cc) cooled to 0° C. The reaction is continued for 1 hour at 10°–15° C. The reaction medium is added to distilled water (500 cc) and the organic phase extracted with dichloromethane (3×100 cc). After washing with 1N hydrochloric acid (2×50 cc) and then with distilled water (2×50 cc), drying over magnesium sulphate and concentration to dryness under reduced pressure (20 mm Hg; 2.7 kPa), 2-(2-trifluoroacetylimino-6-trifluoromethoxy-3-benzothiazolinyl)ethyl p-toluenesulphonate (14.1 g), m.p. 143° C., is obtained.

2-(2-Trifluoroacetylimino-6-trifluoromethoxy-3-benzothiazolinyl)ethanol may be prepared in the following manner: 2-(2-imino-6-trifluoromethoxy-3-benzothiazolinyl)ethanol hydrobromide (20.7 g), ethyl trifluoroacetate (9.8 g) and triethylamine (16.1 cc) are stirred in ethanol (100 cc) for 22 hours at a temperature in the region of 20° C. After concentration to dryness under reduced pressure, the residue obtained is purified by chromatography on a silica column with ethyl acetate as eluent. 2-(2-Trifluoroacetylimino-6-trifluoromethoxy-3-benzothiazolinyl)ethanol (19.2 g), m.p. 144° C., is obtained.

2-(2-Imino-6-trifluoromethoxy-3-benzothiazolinyl)ethanol may be prepared according to the following process: 2-amino-6-trifluoromethoxybenzothiazole (9.4 g) and 2-bromoethanol (10 g) in absolute ethanol (30 cc) are heated for 95 hours to boiling. The mixture is then cooled to a temperature in the region of 20° C. The precipitate formed is filtered off and washed with ethyl ether (100 cc). 2-(2-Imino-6-trifluoromethoxy-3-benzothiazolinyl)ethanol hydrobromide (6.4 g), m.p. 219° C., is obtained.

2-Amino-6-trifluoromethoxybenzothiazole may be prepared according to the method described by L. M. YAGUPOL'SKII et al., Zh. Obahch. Khim, 33(7), 2301 (1963).

EXAMPLE 7

The procedure is as in Example 6, starting with sodium hydride (0.8 g) in 50% strength dispersion in liquid paraffin, 2-pyridylmethyl mercaptan (1.9 g) 2-(2-trifluoroacetylimino-6-trifluoromethoxy-3-benzothiazolinyl)ethyl paratoluenesulphonate (0.8 g) and dimethylformamide (30 cc). The mixture is stirred for 12 hours at a temperature in the vicinity of 20° C. Ethanol (50 cc), water (10 cc) and concentrated ammonia solution (10N) (20 cc) are added, in that order, to this solution. The solution is brought to reflux for 1 hour and cooled to a temperature in the region of 20° C. This aqueous solution is extracted with dichloromethane (2×50 cc), dried over anhydrous magnesium sulphate, filtered and concentrated to dryness at 40° C. under reduced pressure (20 mm Hg; 2.7 kPa). The residue obtained is purified by flash chromatography on a silica column under a stream of nitrogen at moderate pressure (0.5–1.5 bars), with a mixture of cyclohexane and ethyl acetate (50:50 by volume) as eluent. 2-Imino-3-[2-(2-pyridylmethylthio)ethyl]-6-trifluoromethoxybenzothiazoline (3.5 g), m.p. 125° C., is thereby isolated.

EXAMPLE 8 meta-Chloroperbenzoic acid (90% pure by weight) (1 g) is added in the course of ten minutes at a temperature in the region of −10° C., with stirring, to 2-imino-3-[2-(2pyridylthio)ethyl]-6-trifluoromethoxy-benzothiazoline (1.9 g) dissolved in chloroform (30 cc). The reaction mixture is stirred for 1 hour at a temperature in the region of 20° C. and then concentrated at 40° C. under reduced pressure (20 mm Hg; 2.7 kPa). The residue is purified by flash chromatography on a silica column under a stream of nitrogen at moderate pressure (0.5–1.5 bars), with a mixture of ethyl acetate and cyclohexane (70:30 by volume) as eluent. The oil thereby obtained is taken up with diethylether (50 cc) and (RS)-2-imino-3-[2-(2-pyridylsulphinyl)ethyl]-6-trifluoromethoxybenzothiazoline (1 g), m.p. 94° C., is isolated.

2-Imino-3-[2-(2-pyridylthio)ethyl]-6-trifluoromethoxybenzothiazoline may be prepared in the following manner: the procedure is as in Example 6, starting with sodium hydride (1.6 g) in 50% strength dispersion in liquid paraffin, 2-mercaptopyridine (3.6 g), 2-(2-trifluoroacetylamino-6-trifluoromethoxy-3-benzothiazolinyl)ethyl paratoluenesulphonate (16 g) and dimethylformamide (30 cc). The mixture is stirred for 12 hours at a temperature in the vicinity of 20° C. Ethanol (50 cc), water (10 cc) and concentrated ammonia solution (10N) (20 cc) are added, in that order, to this solution. The solution is brought to reflux for 1 hour and cooled to a temperature in the region of 20° C. This aqueous solution is extracted with dichloromethane (2×50 cc), dried over anhydrous magnesium sulphate, filtered and concentrated to dryness at 40° C. under reduced pressure (20 mm Hg; 2.7 kPa). The residue is taken up with isopropyl ether (40 cc) and hexane (80 cc). 2-Imino-3-[2-(2-pyridylthio)ethyl]-6-trifluoromethoxy-benzothiazoline (8 g), m.p. 104° C., is thereby isolated directly.

EXAMPLE 9 m-Chloroperbenzoic acid (0.6 g) is added in the course of approximately 10 minutes to 2-imino-3-(2-phenylthioethyl)-6-trifluoromethoxybenzothiazoline (1.3 g) in absolute ethanol (20 cc) cooled to 0° C. The reaction is continued for 3 hours at a temperature in the region of 20° C. The reaction medium is concentrated to dryness under reduced pressure (20 mm Hg; 2.7 kPa) and the residue obtained purified by chromatography on a silica column with ethyl acetate as eluent. (RS)-2-Imino-3-(2-phenylsulphinylethyl)-6-trifluoromethoxybenzothiazoline (0.7 g) is obtained in the form of a yellowish oil, which is converted to a hydrochloride, m.p. 210° C.

EXAMPLE 10

1-Bromo-2-butyne (10 g), 2-amino-6-trifluoromethoxybenzothiazole (17 g) and ethanol (30 cc) are heated to reflux for 6 hours. After the mixture has returned to a temperature in the region of 20° C., the ethanol is evaporated off under reduced pressure (20 mm Hg; 2.7 kPa) and the red solid obtained is taken up with water (100 cc), alkalinized with 28% strength ammonia solution and extracted with ethyl acetate (300 cc in total). The organic extract is dried over magnesium sulphate, filtered and evaporated under reduced pressure (20 mm Hg; 2.7 kPa). The evaporation residue is purified by chromatography on a silica column with a mixture of cyclohexane and ethyl acetate (60:40 by volume) as eluent: a cream solid (7.2 g) is obtained, which solid is recrystallized in a mixture of cyclohexane (100 cc) and ethyl acetate (5 cc) to yield 3-(2-butynyl)-2-imino-6-trifluoromethoxybenzothiazoline (5.1 g), m.p. 116° C.

1-Bromo-2-butyne may be prepared according to the method described in BEILSTEIN 1, IV 1974.

2-Amino-6-trifluoromethoxybenzothiazole may be obtained according to the method described by L. M. YAGUPOL'SKII et al., Zh. Obsch. Khim., 33(7), 2301 (1963).

EXAMPLE 11

The procedure is as in Example 10, starting with 4-bromo-1-butyne (16 g) and 2-amino-6-trifluoromethoxybenzothiazole (16 g), which are heated to reflux for 5 hours. After purification by chromatography on a silica column with a mixture of cyclohexane and ethyl acetate (50:50 by volume) as eluent, a white solid (1 g) is obtained, which solid is ground in petroleum ether (40°–65° C.) (6 cc), filtered and dried at 40° C. under reduced pressure (3 mm Hg; 0.4 kPa) to give, finally, 3-(3-butynyl)-2-imino-6-trifluoromethoxybenzothiazoline (0.7 g), m.p. 73° C.

4-Bromo-1-butyne may be prepared according to the method described in BEILSTEIN 1, IV 970.

EXAMPLE 12

2-Amino-6-trifluoromethoxybenzothiazole (9.4 g) and 2-chloro-1-dimethylaminopropane hydrochloride (7.0 g) are heated for 1 hour to 130° C. 2-Propanol (20 cc) is added an heating is continued for 24 hours to boiling. After cooling of the mixture to a temperature in the region of 20° C., the precipitate is filtered off and then treated with 1N sodium hydroxide (80 cc) in distilled water (100 cc). The residue obtained by extraction with dichloromethane, drying over magnesium sulphate and concentration to dryness under reduced pressure (20 mm Hg; 2.7 kPa) is purified by chromatography on a silica column with a mixture of ethyl acetate and methanol (80:20 by volume) as eluent. (RS)-3-(2-Dimethylaminopropyl)-2-imino-6-trifluoromethoxybenzothiazoline (3.3 g) is obtained in the form of a yellow oil, which is converted to a dihydrochloride subliming at about 190° C.

EXAMPLE 13

A mixture of 2-amino-6-trifluoromethoxybenzothiazole (9.4 g), 1-chloro-2-(4-fluorophenylthio)ethane (15.2 g) and sodium iodide (12 g) in methyl ethyl ketone (30 cc) is heated 48 hours to boiling. After cooling of the mixture to a temperature in the region of 20° C., ethyl ether (50 cc) is added and the precipitate obtained is filtered off. The latter is taken up in distilled water (100 cc) and treated with 1N sodium hydroxide (10 cc). After extraction with dichloromethane (100 cc), drying over magnesium sulphate and concentration under reduced pressure (20 mm Hg; 2.7 kPa), 2-imino-3-[2-(4-fluorophenylthio)ethyl]-2-imino-6-trifluoromethoxybenzothiazoline (1.4 g) is obtained in the form of a yellow oil, which is converted to a hydrochloride, m.p. 200° C.

1-Chloro-2-(4-fluorophenylthio)ethane may be prepared according to the method described by H. P. S. CHAWLA et al., J. Med. Chem., 13 (3), 480 (1970).

EXAMPLE 14

A mixture of 2-amino-6-trifluoromethoxybenzothiazole (5.9 g), 1-chloro-2-(2,2,2-trifluoro-ethylthio)ethane (4.8 g) and sodium iodide (3.8 g) in methyl ethyl ketone (20 cc) is heated for 72 hours to boiling and then cooled to a temperature in the region of 20° C. After the addition of ethyl ether (100 cc), the precipitate formed is filtered off and the filtrate concentrated to dryness under reduced pressure (20 mm Hg; 2.7 kPa). The residue obtained is taken up in ethyl acetate (20 cc) and the hydrochloride formed by adding 4.2N ethereal hydrogen chloride (7 cc). 2-Imino-3-[2-(2,2,2-trifluoroethylthio)ethyl]-6-trifluoromethoxy-benzothiazoline hydrochloride (1.2 g), subliming at about 180° C., is obtained.

1-Chloro-2-(2,2,2-trifluoroethylthio)ethane may be prepared according to the following process: 2-(2,2,2-trifluoroethylthio)ethanol (13.1 g) and triphenylphosphine (27.8 g) in carbon tetrachloride (60 cc) are heated for 3 hours to boiling. After cooling of the mixture to 0° C., cyclohexane (70 cc) is added, the precipitate formed is filtered off and the filtrate concentrated to dryness under reduced pressure (20 mm Hg; 2.7 kPa). The residue obtained is purified by distillation. 1-Chloro-2-(2,2,2-trifluoroethylthio)ethane (4.8 g), b.p. 105° C. at 200 mm Hg, is obtained.

2-(2,2,2-Trifluoroethylthio)ethanol may be prepared according to the following method: sodium (6.1 g) is added gradually to absolute ethanol (170 cc) at a temperature in the region of 20° C. 2-Mercaptoethanol (18.6 cc) is added in the course of approximately 30 minutes to the sodium ethylate thereby formed, followed by the addition of trifluoroethyl iodide (25.9 cc). The reaction mixture is brought to boiling for 30 minutes and then concentrated to dryness under reduced pressure. The residue obtained is taken up with ethyl ether (300 cc), the precipitate formed is filtered off and the filtrate washed with distilled water (3×200 cc). After drying over magnesium sulphate and concentration to dryness under reduced pressure, 2-(2,2,2-trifluoroethylthio)ethanol (22.6 g) is obtained in the form of a colourless oil.

EXAMPLE 15

2-Amino-6-trifluoromethoxybenzothiazole (7.1 g) and methyl iodide (4.3 g) in absolute ethanol (20 cc) are heated for 18 hours to boiling. The mixture is then cooled to a temperature in the region of 20° C. The precipitate formed is separated by filtration and washed with absolute ethanol (2×20 cc). The solid is taken up in distilled water (100 cc) heated to 60° C., and the solution obtained is treated with sodium hydrogen carbonate (2.6 g). The precipitate is separated by filtration and recrystallized in a boiling mixture (50 cc) of absolute ethanol and distilled water (50:50 by volume). 2-Imino-3-methyl-6-trifluoromethoxybenzothiazoline (2.1 g), m.p. 60°-62° C., is obtained.

2-Amino-6-trifluoromethoxybenzothiazole may be prepared according to the method described by L. M. YAGUPOL'SKII et al., Zh. Obshch. Khim., 33(7), 2301 (1963).

EXAMPLE 16

The procedure is as in Example 15, starting with 2-amino-6-trifluoromethoxybenzothiazole (9.4 g) and ethyl iodide (6.2 g) in absolute ethanol (30 cc). The mixture is heated for 51 hours to boiling and then cooled to a temperature in the region of 20° C. The precipitate is separated by filtration, treated with 1N sodium hydroxide (20 cc) in distilled water (50 cc) and then extracted with ethyl acetate (200 cc). After concentration to dryness at 40° C. under reduced pressure (20 mm Hg; 2.7 kPa), the residue is taken up in ethyl ether (30 cc) and treated with 4.2N ethereal hydrogen chloride (3.1 cc). 3-Ethyl-2-imino-6-trifluoromethoxybenzothiazoline hydrochloride (3.5 g), m.p. 234° C., is obtained.

EXAMPLE 17

The procedure is as in Example 15, starting with 2-amino-6-trifluoromethoxybenzothiazole (7 g) and 1-iodopropane (10.2 g) in absolute ethanol (20 cc). The mixture is heated for 42 hours to boiling. After cooling to a temperature in the region of 20° C., the reaction mixture is concentrated to dryness at 50° C. under reduced pressure (20 mm Hg; 2.7 kPa) and the residue treated with sodium carbonate (3.2 g) in distilled water. After extraction with ethyl acetate (200 cc) and purification by chromatography on a silica column with a mixture of ethyl ether and cyclohexane (65:35 by volume) as eluent, 2-imino-3-propyl-6-trifluoromethoxybenzothiazoline (1.3 g), converted to a hydrochloride subliming at about 180° C., is obtained.

EXAMPLE 18

The procedure is as in Example 15, starting with 2-amino-6-trifluoromethoxybenzothiazole (9.4 g) and allyl bromide (9.6 g) in absolute ethanol (30 cc). The mixture is heated for 48 hours to boiling. After cooling of the mixture to 0° C., the precipitate is filtered off, washed with ethyl ether (200 cc) and recrystallized in boiling 2-propanol (70 cc). 3-Allyl-2-imino-6-trifluoromethoxybenzothiazoline hydrobromide (4 g), m.p. 225° C., is obtained.

EXAMPLE 19

The procedure is as in Example 15, starting with 2-amino-6-trifluoromethoxybenzothiazole (9.4 g) and 4-bromo-1-butene (10.8 g) in 2-propanol (30 cc). The mixture is heated for 48 hours to boiling. After cooling of the mixture to a temperature in the region of 20° C., the precipitate is filtered off and then washed with 2-propanol (2×50 cc). 3-(3-Butenyl)-2-imino-6-trifluoromethoxybenzothiazoline hydrobromide (2.5 g), m.p. 202° C., is obtained.

EXAMPLE 20

The procedure is as in Example 15, starting with 2-amino-6-trifluoromethoxybenzothiazole (9.4 g) and bromomethylcyclopropane (12.7 g) in 2-propanol (30 cc). The mixture is heated for 42 hours to boiling. After cooling of the reaction medium to a temperature in the region of 20° C., the precipitate is filtered off and recrystallized in a boiling mixture (30 cc) of ethyl acetate and methanol (80:20 by volume). 3-Cyclopropylmethyl- 2-imino-6-trifluoromethoxybenzothiazoline hydrobromide (1.2 g), m.p. 220° C., is obtained.

EXAMPLE 21

2-Amino-6-trifluoromethoxybenzothiazole (9.4 g), N-(2-chloroethyl)acetamide (9.7 g) and sodium iodide (13.5 g) in methyl ethyl ketone (30 cc) are heated for 40 hours to boiling. After cooling to a temperature in the region of 20° C., the reaction medium is added to distilled water (200 cc), treated with 1N sodium hydroxide (40 cc) and then extracted with ethyl acetate (200 cc). After drying over magnesium sulphate and then concentration to dryness at 40° C. under reduced pressure (20 mm Hg; 2.7 kPa), the residue is purified by chromatography on a silica column with a mixture of ethyl acetate and methanol (90:10 by volume) as eluent. 3-(2-Acetamidoethyl)-2-imino-6-trifluoromethoxybenzothiazoline (2.7 g) is obtained, which product is converted to a hydrochloride subliming at about 180° C.

EXAMPLE 22

The procedure is as in Example 15, starting with 2-amino-6-trifluoromethoxybenzothiazole (9.4 g) and iodoacetamide (14.8 g) in methyl ethyl ketone (50 cc). The mixture is heated for 18 hours to boiling and then cooled to a temperature in the region of 20° C. The precipitate formed is filtered off, then added to distilled water (100 cc) and treated with 1N sodium hydroxide (37 cc). The insoluble matter is filtered off, washed with distilled water (100 cc) and recrystallized in boiling methanol (100 cc). (2-Imino-6-trifluoromethoxy-3-benzothiazolinyl)acetamide (6.2 g), m.p. 228° C., is obtained.

EXAMPLE 23

The procedure is as in Example 21, starting with 2-amino-6-trifluoromethoxybenzothiazole (9.4 g), N,N-diethylchloroacetamide (12 g) and sodium iodide (13.5 g) in methyl ethyl ketone (30 cc). The mixture is heated for 16 hours to boiling and then cooled to a temperature in the region of 20° C. The reaction medium is added to distilled water (100 cc), treated with 1N sodium hydroxide (50 cc) and then extracted with ethyl acetate (150 cc). After drying over magnesium sulphate and then concentrating to dryness at 40° C. under reduced pressure (20 mm Hg; 2.7 kPa), the residue is purified by chromatography on a silica column with ethyl acetate as eluent. N,N-Diethyl-(2-imino-6-trifluoromethoxy-3-benzothiazolinyl)acetamide (4.2 g) is obtained, which product is converted to a hydrochloride, m.p. 223° C.

EXAMPLE 24

The procedure is as in Example 21, starting with 2-amino-6-trifluoromethoxybenzothiazole (9.4 g), 1-chloro-2-phenylthioethane (13.8 g) and sodium iodide (13.5 g) in methyl ethyl ketone (30 cc). The mixture is heated for 88 hours to boiling and then cooled to a temperature in the region of 20° C. Ethyl ether (250 cc) is added to the reaction medium and the precipitate formed is filtered off. The solid is suspended in distilled water (250 cc), treated with 1N sodium hydroxide (40 cc) and then extracted with ethyl ether (100 cc). After drying over magnesium sulphate and filtration, ethyl acetate (150 cc) is added to the filtrate, which is treated with 4N ethereal hydrogen chloride (10 cc). The precipitate formed is filtered off and recrystallized in 2-propanol (85 cc). 2-Imino-3-(2-phenylthioethyl)-6-trifluoromethoxybenzothiazoline hydrochloride (5.4 g), m.p. 174° C., is obtained.

EXAMPLE 25

The procedure is as in Example 15, starting with 2-amino-6-trifluoromethoxybenzothiazole (9.4 g) and 2-bromoethanol (10 g) in absolute ethanol (30 cc). The mixture is heated for 95 hours to boiling and then cooled to a temperature in the region of 20° C. The precipitate formed is filtered off and washed with ethyl ether (100 cc). 2-(2-Imino-6-trifluoromethoxy-3-benzothiazolinyl)ethanol hydrobromide (6.4 g), m.p. 219° C., is obtained.

EXAMPLE 26

The procedure is as in Example 8, starting with 2-imino-3-[2-(2-pyrimidinylthio)ethyl]-6-trifluoromethoxybenzothiazoline (0.5 g) and meta-chloroperbenzoic acid (90% pure by weight) (1 g) dissolved in chloroform (20 cc). The reaction mixture is stirred for 1 hour at a temperature in the region of 20° C. and then concentrated to dryness at 40° C. under reduced pressure (20 mm Hg; 2.7 kPa). The residue is purified by flash chromatography on a silica column under a stream of nitrogen at moderate pressure (0.5–1.5 bars), with a mixture of ethyl acetate and methanol (95:5 by volume) as eluent. 2-Imino-3-[2-(2-pyrimidinylsulphinyl)ethyl]-6-trifluoromethoxybenzothiazoline (0.35 g), m.p. 120° C., is isolated.

2-Imino-3-[2-(2-pyrimidinylthio)ethyl]-6-trifluoromethoxybenzothiazoline may be prepared in the following manner: the procedure is as in Example 6 for the preparation of 2-imino-3-[2-(2-pyridylthio)ethyl]-6-trifluoromethoxybenzothiazoline, starting with sodium hydride (0.8 g) in 50% strength dispersion in liquid paraffin, 2-mercaptopyrimidine (1.8 g), 2-(2-trifluoroacetylimino-6-trifluoromethoxy-3-benzothiazolinyl)ethyl para-toluenesulphonate (8 g) and dimethylformamide (100 cc). The mixture is stirred for 12 hours at a temperature in the vicinity of 20° C. Ethanol (100 cc), water (50 cc) and concentrated ammonia solution (10N) (50 cc) are then added, in that order, to this solution. The solution is brought to reflux for one hour and cooled to a temperature in the region of 20° C. This solution is extracted with dichloromethane (2×100 cc) and the combined extracts are dried over anhydrous magnesium sulphate, filtered and concentrated to dryness at 40° C. under reduced pressure (20 mm Hg; 2.7 kPa). The oil thereby obtained is purified by flash chromatography on a silica column under a stream of nitrogen at moderate pressure (0.5–1.5 bars), with a mixture of ethyl acetate and cyclohexane (50:50 by volume) as eluent. 2-Imino-3-[2-(2-pyrimidylthio)ethyl]-6-trifluoromethoxybenzothiazoline (2.4 g), m.p. 110° C., is isolated.

EXAMPLE 27

The procedure is as in Example 8, starting with 2-imino-3-[2-(4-pyridylthio)ethyl)]-6-trifluoromethoxybenzothiazoline (2 g) and meta-chloroperbenzoic acid (90% pure by weight) (0.68 g) dissolved in water (25 cc) and dioxane (25 cc). The reaction mixture is stirred for 12 hours at 25° C. and then concentrated to dryness at 40° C. under reduced pressure (20 mm Hg; 2.7 kPa) to remove the dioxane. The aqueous solution is taken to a pH of 12–13 with concentrated ammonia solution (10N) and then extracted with dichloromethane (2×50 cc). The organic phase is dried over anhydrous magnesium sulphate and concentrated to dryness at 40° C. under reduced pressure (20 mm Hg; 2.7 kPa). The oil thereby obtained is purified by flash chromatography on a silica column under a stream of nitrogen at moderate pressure (0.5–1.5 bars), with a mixture of ethyl acetate and methanol (90:10 by volume) as eluent. An oil is thereby isolated, which oil, when treated with oxalic acid (0.25 g) and acetone (5 cc), gives 2-imino-3-[2-(4-pyridylsulphinyl)ethyl]-6-trifluoromethoxybenzothiazoline (0.9 g) directly in the form of an oxalate, m.p. 194° C.

The present invention also provides pharmaceutical compositions comprising at least one compound of formula (I), or a salt of such a compound, in the pure state or in the form of a composition in which it is combined with any other pharmaceutically compatible product, which can be inert or physiologically active, and in particular with a compatible pharmaceutically acceptable carrier. The pharmaceutical compositions of the invention may be employed orally, parenterally, rectally or topically.

As solid compositions for oral administration, tablets, pills, powders (gelatin capsules, wafer capsules) or granules may be used. In these compositions, the active principle according to the invention is mixed with one or more inert diluents such as starch, cellulose, sucrose, lactose or silica.

These compositions can also comprise substances other than diluents, e.g. one or more lubricants such as magnesium stearate or talc, a colouring, a coating (dragees) or a varnish.

As liquid compositions for oral administration, solutions, suspensions, emulsions, syrups and elixirs of a pharmaceutically acceptable nature, containing inert diluents such as water, ethanol, glycerol, vegetable oils or liquid paraffin, may be used. These compositions can comprise substances other than diluents, e.g. wetting products, sweeteners, thickeners, flavourings or stabilizers.

The sterile compositions for parenteral administration can preferably be suspensions, emulsions or nonaqueous solutions. As a solvent or vehicle, water, propylene glycol, a polyethylene glycol, vegetable oils, especially olive oil, injectable organic esters, e.g. ethyl oleate, or other suitable organic solvents may be employed. These compositions can also contain adjuvants, especially wetting agents, tonicity regulators, emulsifiers, dispersants and stabilizers. The sterilization may be carried out in several ways, e.g. by aseptic filtration, by incorporating sterilizing agents in the composition, by irradiation or by heating. They may also be prepared in the form of sterile solid compositions which can be dissolved at the time of use in sterile water or any other sterile injectable medium.

The compositions for rectal administration are suppositories or rectal capsules which contain, apart from the active products, excipients such as cocoa butter, semi-synthetic glycerides or polyethylene glycols.

The compositions for topical administration can be, e.g., creams, ointments, lotions, eye washes, mouth washes, nasal drops or aerosols.

In human therapy, the compounds according to the invention are especially useful in the treatment and prevention of convulsive phenomena, schizophrenic disorders, and in particular the deficiency forms of schizophrenia, sleep disorders, phenomena linked to cerebral ischaemia and neurological conditions in which glutamate may be implicated, such as Alzheimer's disease, Huntington's chorea, amyotrophic lateral sclerosis and olivopontocerebellar atrophy.

The doses depend on the effect sought, the treatment period and the administration route used; they are generally between 30 and 300 mg per day in oral administration for an adult, with unit doses ranging from 10 to 100 mg of active substance.

Generally speaking, the doctor will determine the appropriate dosage in accordance with the age and weight and all other factors characteristic of the subject to be treated.

The examples which follow illustrate compositions according to the invention.

EXAMPLE A

Hard gelatin capsules containing 50 mg of active product and having the following composition are prepared according to the usual technique:

| | |
|---|---|
| 2-imino-3-(2-cyanoethyl)-6-trifluoromethoxybenzothiazoline | 50 mg |
| cellulose | 18 mg |
| lactose | 55 mg |
| colloidal silica | 1 mg |
| carboxymethylstarch sodium | 10 mg |
| talc | 10 mg |
| magnesium stearate | 1 mg |

EXAMPLE B

Tablets containing 50 mg of active product having the following composition are prepared according to the usual technique:

| | | |
|---|---|---|
| 2-(2-imino-6-trifluoromethoxy-3-benzo-thiazolinyl)ethanesulphonamide | | 50 mg |
| lactose | | 104 mg |
| cellulose | | 40 mg |
| polyvidone | | 10 mg |
| carboxymethylstarch sodium | | 22 mg |
| talc | | 10 mg |
| magnesium stearate | | 2 mg |
| colloidal silica | | 2 mg |
| mixture of hydroxymethylcellulose, glycerol and titanium oxide (72:3.5:24.5) | q.s. 1 finished film-coated tablet weighing | 245 mg |

EXAMPLE C

An injectable solution containing 10 mg of active product and having the following composition is prepared:

| | |
|---|---|
| 2-imino-3-[2-(2-pyridylsulphinyl)ethyl]-6-trifluoromethoxybenzothiazoline | 10 mg |
| benzoic acid | 80 mg |
| benzyl alcohol | 0.06 cc |
| sodium benzoate | 80 mg |
| ethanol, 95% | 0.4 cc |
| sodium hydroxide | 24 mg |
| propylene glycol | 1.6 cc |
| water | q.s. 4 cc |

Although the invention has been described in conjunction with specific embodiments, it is evident that many alternatives and variations will be apparent to those skilled in the art in light of the foregoing description. Accordingly, the invention is intended to embrace all of the alternatives and variations that fall within the

We claim:
1. A compound of the formula:

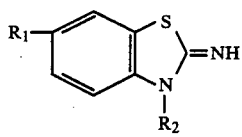

and its pharmaceutically acceptable salts which are nontoxic, in which $R_1$ represents polyfluoroalkoxy, and $R_2$ represents alkyl, alkenyl (3-6 C), (cycloalkyl-(3-6 C))alkyl, carbamoylalkyl, dialkycarbamoylalkyl, acetylaminoalkyl, phenylthioalkyl, hydroxyalkyl, cyanoalkyl, suphamoylethyl, N-alkylsulphamoylethyl, alkynyl (3-6 C), phenylsulphinylalkyl, halophenylthioalkyl, (2,2,2-trifluoroethylthio)alkyl, 2-dialkylaminopropyl, halophenylsulphinylalkyl or (2,2,2-trifluoroethylsulphinyl)alkyl radical, the said alkyl radicals and alkyl and alkoxy portions containing 1 to 4 carbon atoms each in a straight or branched chain.

2. A compound according to claim 1, in which $R_1$ represents trifluoromethoxy, pentafluoroethoxy, 2,2,2-trifluoroethoxy, 1,1,2,2,-tetrafluoroethoxy or 2,2,3,3,3-pentafluoropropoxy.

3. A pharmaceutical composition which comprises, as active principle, at least one compound according to claim 1, or a salt of such a compound with an inorganic or organic acid, and a compatible pharmaceutically acceptable carrier.

4. A method for the treatment of a medical condition associated with the effects of glutamate which comprises administering to a subject in need of such treatment an amount of a compound according to claim 1, or salt thereof sufficient to inhibit such effects at least partially.

5. A compound as claimed in claim 1 which is 2-imino-3-(2-cyanoethyl)-6-trifluoromethoxybenzothiazoline or its addition salts.

6. A compound as claimed in claim 1 which is N-methyl-2-(2-imino-6-trifluoromethyoxy-3-benzothiazolinyl) ethanesul phonamide or its addition salts.

* * * * *